(12) United States Patent
Champagne et al.

(10) Patent No.: US 10,098,680 B2
(45) Date of Patent: Oct. 16, 2018

(54) METACARPAL BONE STABILIZATION DEVICE

(71) Applicant: Exsomed Holding Company LLC, Scottsdale, AZ (US)

(72) Inventors: Lloyd P. Champagne, Phoenix, AZ (US); Jozef Zoldos, Phoenix, AZ (US)

(73) Assignee: Exsomed Holding Company LLC, Scottsdale, AZ (US)

( * ) Notice: Subject to any disclaimer, the term of this patent is extended or adjusted under 35 U.S.C. 154(b) by 27 days.

(21) Appl. No.: 15/189,845

(22) Filed: Jun. 22, 2016

(65) Prior Publication Data

US 2016/0296264 A1 Oct. 13, 2016

Related U.S. Application Data

(62) Division of application No. 13/940,173, filed on Jul. 11, 2013, now Pat. No. 9,480,515.

(Continued)

(51) Int. Cl.
*A61B 17/86* (2006.01)
*A61B 17/56* (2006.01)
(Continued)

(52) U.S. Cl.
CPC .......... *A61B 17/8625* (2013.01); *A61B 17/56* (2013.01); *A61B 17/72* (2013.01); *A61B 17/7233* (2013.01); *A61B 17/7291* (2013.01); *A61B 17/84* (2013.01); *A61B 17/846* (2013.01); *A61B 17/86* (2013.01); *A61B 17/863* (2013.01); *A61B 17/8605* (2013.01);
(Continued)

(58) Field of Classification Search
CPC ... A61B 17/56; A61B 2017/564; A61B 17/72; A61B 17/7233; A61B 17/7291; A61B 17/84; A61B 17/846; A61B 17/86; A61B 17/8605; A61B 17/8625; A61B 17/863; A61B 17/8635; A61B 2017/8655; F16B 25/0015; F16B 25/0057
See application file for complete search history.

(56) References Cited

U.S. PATENT DOCUMENTS 1,741,279 A 12/1929 Bowman
2,037,586 A 4/1936 Olson
(Continued)

FOREIGN PATENT DOCUMENTS

CH 643131 5/1984
CH 646858 12/1984
(Continued)

OTHER PUBLICATIONS

USPTO; Final Office Action dated Jun. 2, 2017 in U.S. Appl. No. 14/503,157.
(Continued)

*Primary Examiner* — Larry E Waggle, Jr.
(74) *Attorney, Agent, or Firm* — Snell & Wilmer L.L.P.

(57) ABSTRACT

A device and method for stabilizing a broken bone while it heals is disclosed. The device is preferably a metal rod that has a threaded portion. The device is positioned into a bone, such as a metacarpal bone, by forming an opening in the bone suitable for receiving the device, and inserting it into the opening wherein the threaded portion retains the device in position.

20 Claims, 2 Drawing Sheets

Related U.S. Application Data

(60) Provisional application No. 61/671,021, filed on Jul. 12, 2012.

(51) Int. Cl.
*A61B 17/72* (2006.01)
*A61B 17/84* (2006.01)
*F16B 25/00* (2006.01)
*A61F 2/42* (2006.01)

(52) U.S. Cl.
CPC ...... *A61B 17/8635* (2013.01); *F16B 25/0015* (2013.01); *F16B 25/0057* (2013.01); *A61B 2017/564* (2013.01); *A61B 2017/8655* (2013.01); *A61F 2/4241* (2013.01)

(56) References Cited

U.S. PATENT DOCUMENTS

| | | |
|---|---|---|
| 2,210,455 A | 8/1940 | Hosking |
| 2,217,951 A | 10/1940 | Hosking |
| 2,229,892 A | 1/1941 | Hosking |
| 2,242,003 A | 5/1941 | Lorenzo |
| 3,275,055 A | 9/1966 | Gutshall |
| 3,397,699 A | 8/1968 | Kohl |
| 3,717,146 A | 2/1973 | Halloran |
| 4,380,414 A | 4/1983 | Capuano |
| 4,471,777 A | 9/1984 | McCorkle |
| 4,584,722 A | 4/1986 | Levy et al. |
| 4,608,965 A | 9/1986 | Anspach |
| 4,764,066 A | 8/1988 | Terrell |
| 4,781,191 A | 11/1988 | Thompson |
| 4,812,095 A | 3/1989 | Piacenti |
| 4,901,717 A | 2/1990 | Moore et al. |
| 4,909,789 A | 3/1990 | Taguchi et al. |
| 5,061,283 A | 10/1991 | Silvestrini |
| 5,234,299 A | 8/1993 | Giannuzzi |
| 5,312,255 A | 5/1994 | Bauer |
| 5,345,927 A | 9/1994 | Bonutti |
| 5,443,466 A | 8/1995 | Shah |
| 5,645,545 A | 7/1997 | Bryant |
| 5,667,510 A | 9/1997 | Combs |
| 5,690,633 A | 11/1997 | Taylor et al. |
| 5,853,413 A | 12/1998 | Carter et al. |
| 6,187,007 B1 | 2/2001 | Frigg |
| 6,221,006 B1 | 4/2001 | Dubrul et al. |
| 6,231,319 B1 | 5/2001 | Iida et al. |
| 6,231,413 B1 | 5/2001 | Tsukamoto |
| 6,306,140 B1 | 10/2001 | Siddiqui |
| 6,475,242 B1 | 11/2002 | Bramlet |
| 6,517,541 B1 | 2/2003 | Sesic |
| 6,592,623 B1 | 7/2003 | Bowlin et al. |
| 6,607,530 B1 | 8/2003 | Carl et al. |
| 6,808,526 B1 | 10/2004 | Magerl et al. |
| 7,041,106 B1 | 5/2006 | Carver et al. |
| 7,334,976 B2 | 2/2008 | Dicke |
| 7,465,135 B2 | 12/2008 | Fritsch |
| 7,708,738 B2 | 5/2010 | Fourcault et al. |
| 7,766,942 B2 | 8/2010 | Patterson |
| 7,988,724 B2 | 8/2011 | Salahieh et al. |
| 8,011,866 B2 | 9/2011 | Harris |
| 8,157,803 B1 | 4/2012 | Zirkle, Jr. |
| 8,398,687 B2 | 3/2013 | Vasta et al. |
| 8,414,648 B2 | 4/2013 | Reiley |
| 8,419,776 B2 | 4/2013 | Prandi et al. |
| 8,518,042 B2 | 8/2013 | Winsow et al. |
| 8,568,462 B2 | 10/2013 | Sixto et al. |
| 8,597,337 B2 | 12/2013 | Champagne |
| 8,608,783 B2 | 12/2013 | Graham et al. |
| 8,814,918 B2 | 8/2014 | Orbay et al. |
| 8,852,253 B2 | 10/2014 | Mafi |
| 8,864,804 B2 | 10/2014 | Champagne et al. |
| 8,888,429 B2 | 11/2014 | Pamer |
| 8,906,075 B2 | 12/2014 | Conley et al. |
| 9,017,404 B2 | 4/2015 | Champagne et al. |
| 9,046,120 B2 | 6/2015 | Phua |
| 9,175,715 B2 | 11/2015 | Babej |
| 9,265,600 B2 | 2/2016 | Niese |
| 9,480,515 B2 | 11/2016 | Champagne |
| 9,539,084 B2 | 1/2017 | Champagne |
| 2001/0049529 A1 | 12/2001 | Cachia et al. |
| 2002/0045897 A1 | 4/2002 | Dixon et al. |
| 2002/0055747 A1 | 5/2002 | Cano et al. |
| 2002/0055749 A1 | 5/2002 | Esnouf et al. |
| 2002/0143337 A1 | 10/2002 | Orbay et al. |
| 2002/0198527 A1 | 12/2002 | Muckter |
| 2003/0014077 A1 | 1/2003 | Leung |
| 2003/0083661 A1 | 5/2003 | Orbay et al. |
| 2003/0130735 A1 | 7/2003 | Rogalski |
| 2004/0193217 A1 | 9/2004 | Lubbers |
| 2004/0210227 A1 | 10/2004 | Trail et al. |
| 2004/0260288 A1 | 12/2004 | Means |
| 2005/0075642 A1 | 4/2005 | Felt et al. |
| 2005/0107791 A1 | 5/2005 | Manderson |
| 2005/0143735 A1 | 6/2005 | Kyle |
| 2006/0129153 A1 | 6/2006 | Klaue et al. |
| 2006/0149249 A1 | 7/2006 | Mathoulin et al. |
| 2006/0165506 A1 | 7/2006 | Panasik |
| 2006/0195099 A1 | 8/2006 | Bottlang |
| 2006/0271061 A1 | 11/2006 | Beyar |
| 2006/0276790 A1 | 12/2006 | Dawson |
| 2007/0027547 A1 | 2/2007 | Rydell et al. |
| 2007/0135816 A1 | 6/2007 | Kropf et al. |
| 2007/0282342 A1 | 12/2007 | Niederberger et al. |
| 2007/0299449 A1* | 12/2007 | Allinniemi ......... A61B 17/0401 606/232 |
| 2008/0183220 A1 | 7/2008 | Glazer |
| 2008/0219801 A1* | 9/2008 | Toenjes ............... F16B 25/0015 411/413 |
| 2008/0249547 A1 | 10/2008 | Dunn |
| 2008/0249574 A1 | 10/2008 | McCombs et al. |
| 2009/0062868 A1 | 3/2009 | Casutt |
| 2009/0299369 A1 | 12/2009 | Orbay et al. |
| 2010/0106254 A1 | 4/2010 | Delsignore |
| 2010/0121136 A1 | 5/2010 | Champagne |
| 2010/0130978 A1 | 5/2010 | Orbay et al. |
| 2010/0211115 A1* | 8/2010 | Tyber .................. A61B 17/863 606/305 |
| 2010/0312286 A1 | 12/2010 | Dell'Oca |
| 2010/0324556 A1 | 12/2010 | Tyber et al. |
| 2011/0009865 A1* | 1/2011 | Orfaly ................ A61B 17/1717 606/62 |
| 2011/0130794 A1 | 6/2011 | Vaidya |
| 2012/0083847 A1 | 4/2012 | Heubner et al. |
| 2012/0136398 A1 | 5/2012 | Mobasser |
| 2012/0191140 A1 | 7/2012 | Bonutti |
| 2012/0221104 A1 | 8/2012 | Altman et al. |
| 2012/0253464 A1 | 10/2012 | Hwang et al. |
| 2012/0253465 A1 | 10/2012 | Missos |
| 2013/0053961 A1 | 2/2013 | Derwin et al. |
| 2013/0060333 A1 | 3/2013 | Gonzalez |
| 2013/0131699 A1 | 5/2013 | Jiang et al. |
| 2013/0138123 A1 | 5/2013 | Stone et al. |
| 2013/0165979 A1 | 6/2013 | Greenberg et al. |
| 2013/0190872 A1 | 7/2013 | Makower et al. |
| 2013/0197592 A1 | 8/2013 | Mafi |
| 2013/0245626 A1* | 9/2013 | Lavi ..................... A61B 17/72 606/62 |
| 2013/0245700 A1 | 9/2013 | Choinski |
| 2013/0261662 A1 | 10/2013 | Mayer et al. |
| 2013/0274879 A1 | 10/2013 | Champagne et al. |
| 2013/0282058 A1 | 10/2013 | ElAttrache et al. |
| 2013/0325011 A1 | 12/2013 | Cleveland et al. |
| 2014/0025124 A1 | 1/2014 | Champagne et al. |
| 2014/0067063 A1 | 3/2014 | Bonutti |
| 2014/0257349 A1 | 9/2014 | Sudekum |
| 2014/0276846 A1 | 9/2014 | Mauldin |
| 2014/0336712 A1 | 11/2014 | Strnad et al. |
| 2015/0066060 A1 | 3/2015 | Bojarski |
| 2015/0094722 A1 | 4/2015 | Champagne et al. |
| 2015/0094724 A1 | 4/2015 | Champagne et al. |
| 2015/0094777 A1 | 4/2015 | Champagne et al. |
| 2015/0173737 A1 | 6/2015 | Champagne et al. |
| 2015/0182325 A1 | 7/2015 | Champagne et al. |

(56) References Cited

U.S. PATENT DOCUMENTS

| | | | |
|---|---|---|---|
| 2016/0030097 A1 | 2/2016 | Mildner | |
| 2016/0256290 A1 | 9/2016 | Seavey et al. | |
| 2016/0296263 A1 | 10/2016 | Champagne et al. | |
| 2016/0338748 A1 | 11/2016 | Champagne et al. | |
| 2017/0027577 A1 | 2/2017 | Kubiak et al. | |
| 2017/0035553 A1 | 2/2017 | Champagne et al. | |
| 2017/0049167 A1 | 2/2017 | Champagne et al. | |
| 2017/0189090 A1 | 7/2017 | Champagne et al. | |
| 2017/0196609 A1 | 7/2017 | Champagne et al. | |
| 2017/0325827 A1 | 11/2017 | Champagne et al. | |
| 2018/0021124 A1 | 1/2018 | Champagne et al. | |

FOREIGN PATENT DOCUMENTS

| | | |
|---|---|---|
| DE | 2713386 | 11/1978 |
| DE | 102007003645 | 7/2008 |
| DE | 202013101135 | 6/2014 |
| EP | 0597223 | 5/1994 |
| EP | 1378205 | 1/2004 |
| EP | 2606843 | 6/2013 |
| GB | 2007099 | 5/1979 |
| GB | 2181356 | 4/1987 |
| WO | WO199733537 | 9/1997 |
| WO | WO2004093700 | 4/2004 |
| WO | WO2005092226 | 10/2005 |
| WO | WO2006105935 | 12/2006 |
| WO | WO2007081601 | 7/2007 |
| WO | WO2007109140 | 9/2007 |
| WO | WO2008063156 | 5/2008 |
| WO | WO2010151589 | 12/2010 |
| WO | 2012050424 | 4/2012 |
| WO | WO2014011933 | 1/2014 |
| WO | 2015050900 | 4/2015 |
| WO | WO2015050895 | 9/2015 |
| WO | WO2015050896 | 9/2015 |
| WO | WO2015050898 | 9/2015 |
| WO | WO2015050902 | 9/2015 |
| WO | 2016186847 | 11/2016 |

OTHER PUBLICATIONS

USPTO; Final Office Action dated Jun. 13, 2017 in U.S. Appl. No. 14/503,119.
USPTO; Final Office Action dated Aug. 31, 2017 in U.S. Appl. No. 14/503,228.
PCT; International Search Report and Written Opinion dated Sep. 17, 2010 in Application No. PCT/US2009/046662.
EP; Examination Report dated May 30, 2011 in Application No. EP 09774002.1.
USPTO; Office Action dated Oct. 4, 2011 in U.S. Appl. No. 12/372,712.
USPTO; Office Action dated Mar. 21, 2012 in U.S. Appl. No. 12/480,676.
EP; Examination Report dated May 25, 2012 in Application No. EP 09774002.1.
USPTO; Office Action dated May 29, 2012 in U.S. Appl. No. 12/372,712.
USPTO; Office Action dated Sep. 18, 2012 in U.S. Appl. No. 12/480,676.
USPTO; Office Action dated Mar. 22, 2013 in U.S. Appl. No. 12/372,712.
USPTO; Notice of Allowance dated Jul. 30, 2013 in U.S. Appl. No. 12/372,712.
PCT; International Search Report and Written Opinion dated Sep. 9, 2013 in Application No. PCT/US2013/050155.
USPTO; Office Action dated Sep. 24, 2013 in U.S. Appl. No. 12/480,676.
USPTO; Office Action dated Feb. 18, 2014 in U.S. Appl. No. 13/555,933.
USPTO; Notice of Allowance dated Jun. 25, 2014 in U.S. Appl. No. 13/555,933.
USPTO; Office Action dated Aug. 29, 2014 in U.S. Appl. No. 13/648,019.
PCT; International Search Report and Written Opinion dated Dec. 10, 2014 in Application No. PCT/US2014/058463.
PCT; International Search Report and Written Opinion dated Dec. 12, 2014 in Application No. PCT/US2014/058474.
USPTO; Notice of Allowance dated Dec. 31, 2014 in U.S. Appl. No. 13/648,019.
PCT; International Search Report and Written Opinion dated Jan. 20, 2015 in Application No. PCT/US2014/058448.
PCT; International Search Report and Written Opinion dated Feb. 9, 2015 in Application No. PCT/US2014/058441.
USPTO; Office Action dated Dec. 9, 2015 in U.S. Appl. No. 14/640,657.
USPTO; Final Office Action dated May 23, 2016 in U.S. Appl. No. 14/640,657.
USPTO; Office Action dated Sep. 22, 2015 in U.S. Appl. No. 14/503,228.
USPTO; Office Action dated Oct. 5, 2015 in U.S. Appl. No. 13/940,173.
USPTO; Final Office Action dated May 23, 2016 in U.S. Appl. No. 13/940,173.
USPTO; Final Office Action dated May 2, 2016 in U.S. Appl. No. 14/503,228.
USPTO; Notice of Allowance dated Jul. 1, 2016 in U.S. Appl. No. 13/940,173.
USPTO; Notice of Allowance dated Sep. 1, 2016 in U.S. Appl. No. 14/640,657.
USPTO; Non-Final Office Action dated Nov. 4, 2016 in U.S. Appl. No. 14/503,119.
USPTO; Non-Final Office Action dated Jan. 27, 2017 in U.S. Appl. No. 14/503,157.
USPTO; Non-Final Office Action dated Feb. 9, 2017 in U.S. Appl. No. 14/503,228.
USPTO; Non-Final Office Action dated Apr. 10,2017 in U.S. Appl. No. 14/641,024.
PCT; International Search Report and Written Opinion dated Sep. 30, 2014 in Application No. PCT/US2014/058472.
PCT; International Search Report and Written Opinion dated May 4, 2016 in Application No. PCT/US20106/030850.
USPTO; Non-Final Office Action dated Nov. 1, 2017 in U.S. Appl. No. 15/297,698.
USPTO; Non-Final Office Action dated Nov. 30, 2017 in U.S. Appl. No. 15/189,829.
USPTO; Requirement for Restriction dated Nov. 30, 2017 in U.S. Appl. No. 15/214,412.
USPTO; Non-Final Office Action dated Dec. 8, 2017 in U.S. Appl. No. 15/146,824.
USPTO; Non-Final Office Action dated Dec. 15, 2017 in U.S. Appl. No. 14/984,145.
USPTO; Non-Final Office Action dated Feb. 21, 2018 in U.S. Appl. No. 15/151,252.
USPTO; Non-Final Office Action dated Feb. 27, 2018 in U.S. Appl. No. 14/503,157.
USPTO; Non-Final Office Action dated Mar. 5, 2018 in U.S. Appl. No. 14/993,972.
USPTO; Non-Final Office Action dated Mar. 5, 2018 in U.S. Appl. No. 15/214,412.

* cited by examiner

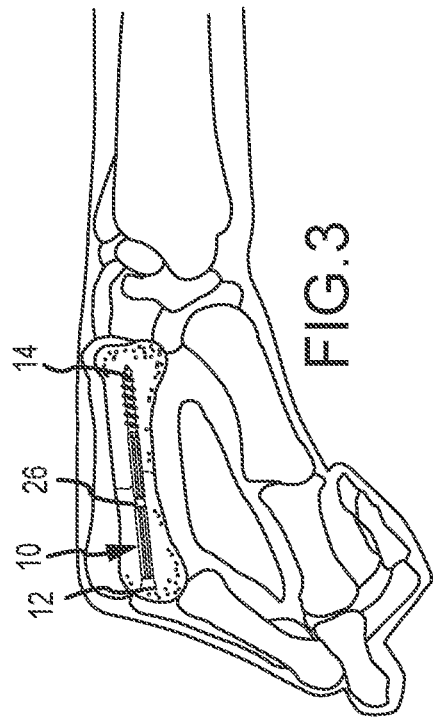
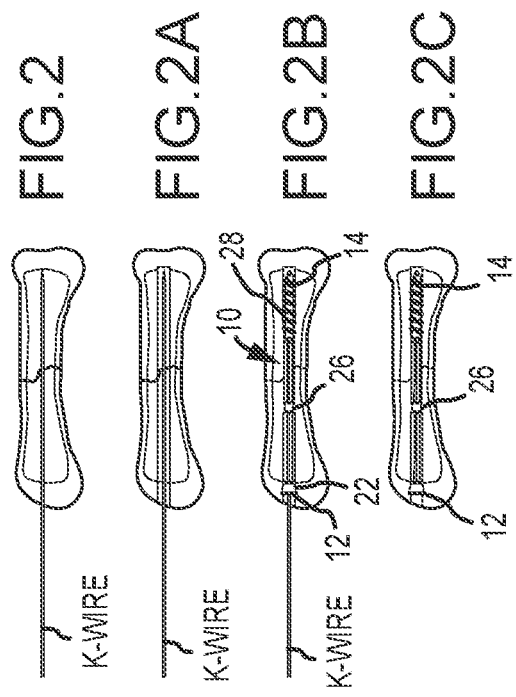
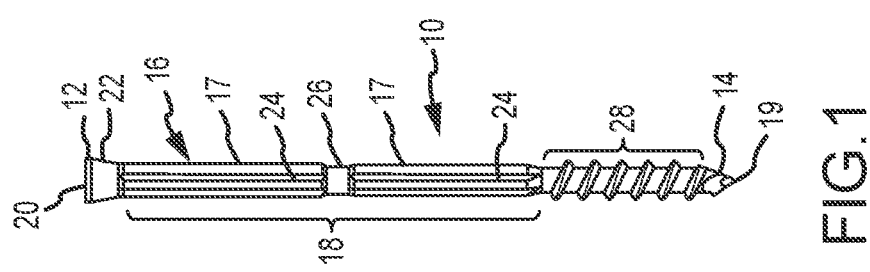

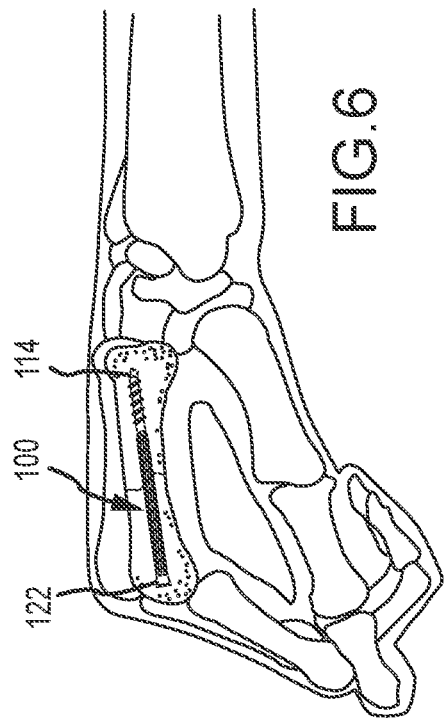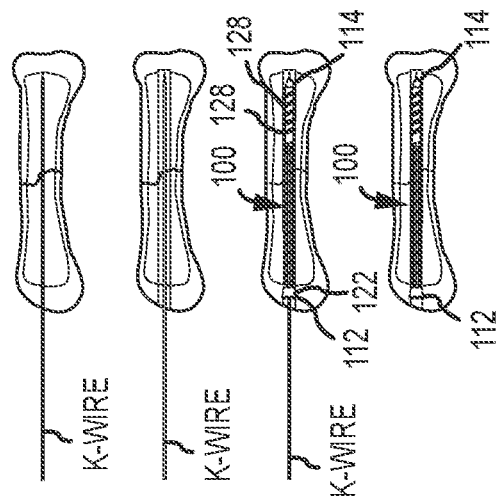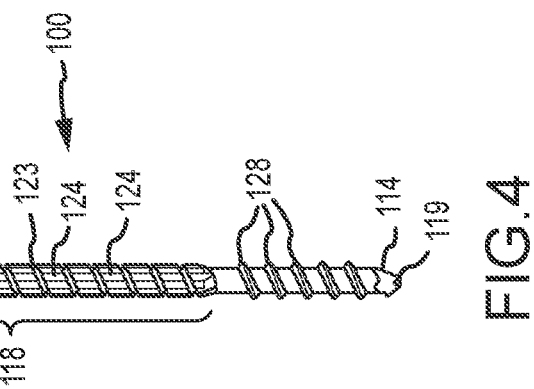

METACARPAL BONE STABILIZATION DEVICE

CROSS-REFERENCE TO RELATED APPLICATIONS

This application is a division of application Ser. No. 13/940,173 filed on Jul. 11, 2013 titled "METACARPAL BONE STABILIZATION DEVICE", which claims priority under 35 U.S.C. 119(e) to U.S. Provisional Patent Application No. 61/671,021, filed Jul. 11, 2012.

FIELD OF THE INVENTION

The present invention relates to a device implantable in a bone to stabilize it while it heals, and which is particularly suitable for use in a metacarpal bone.

BACKGROUND OF THE INVENTION

The palm of the hand is made up of bones called metacarpals, and a metacarpal connects each finger and thumb to the hand. Each finger and thumb is formed of bones called phalanges. The connection of the phalanges to the metacarpals is called a "knuckle" joint or metacarpophalangeal joint (MCP joint), and acts like a hinge when the fingers or thumb are bent.

In each finger, there are three phalanges that are separated by two joints called the interphalangeal joints (IP joints). The proximal IP joint (PIP joint) is the one closest to the MCP joint. The other joint closest to the end of the finger is the distal IP joint (DIP joint). The thumb just has one IP joint. The joints are covered on the ends with articular cartilage.

Damage to the metacarpal bone may occur as a result of a sprain or fracture. Typically, once the metacarpal bone is lined up after an injury it must be stabilized in position while it heals.

To stabilize a broken metacarpal bone, it is now known to use a non-threaded, smooth metal shaft (hereafter "nail") positioned in the metacarpal bone to hold it in position while the bone heals. An opening is first formed in the metacarpal bone, wherein the opening extends through the fracture and the nail is positioned in the opening to provide lateral stability for the parts of the bone on either side of the fracture. After a certain period, a second surgery is required to remove the nail from the bone. Problems with the nail are that, because it is not anchored in the bone, it can migrate through the metacarpal bone and into surrounding tissue. Sometimes this can result in damage to soft tissue, such as a severed or damaged tendon or cartilage, and/or cause pain. Another problem with the nail is that, because it can migrate, a second surgery is required to remove it. Additionally, the proximal end of pins and nails can cause tendon irritation, tendon rupture or skin irritation and infection.

One potential solution to this problem is to insert a screw into the bone. A major problem with such a technique (which to the inventors' knowledge is not utilized and is not prior art) is that the torque required to place a screw into the length of a metacarpal bone (which is a relatively thin, delicate bone) is high. Such a procedure would be lengthy, and there would be a possibility of bone damage, or damage to the driving head of the screw, which could prevent complete insertion into the opening formed in the bone. Current screws are not designed specifically for intramedullary placement. For instance, the current screws are frequently not long enough.

SUMMARY OF THE INVENTION

The present invention solves the problems associated with repairing a metacarpal bone by providing a device that is a unique combination of a nail and a screw, which has threads only along 30% or less of its length. In this manner, the device can be inserted into the bone without damaging the bone because it is only threaded into a small portion of an opening formed in the bone. Further, the device is anchored into the bone, which eliminates migration and eliminates the need for a second operation to remove the device.

The device may have a threaded portion at one or more of its first end, central portion, or second end, and the threaded portion is preferably no greater than 30% and preferably no greater than 20-25% the length of the device. In one embodiment, the threaded area is between 0.5 and 1.5 centimeters ("cm") and most preferably about 1 cm long.

At its first end, or proximal end, the device includes a driving head capable of being driven by any suitable driver into the opening.

BRIEF DESCRIPTION OF THE DRAWINGS

FIG. 1 is a side view of one embodiment of a device according to the invention.

FIGS. 2-2C illustrate one method of utilizing the device of FIG. 1.

FIG. 3 illustrates the device of claim 1 positioned in a metacarpal bone.

FIG. 4 is a side view of an alternate embodiment of a device according to the invention.

FIGS. 5-5C illustrate one method for utilizing the device of FIG. 4.

FIG. 6 illustrates the device of FIG. 4 positioned in a metacarpal bone.

DETAILED DESCRIPTION OF PREFERRED EMBODIMENTS

Turning now to the figures, where the purpose is to describe preferred embodiments of the invention and not to limit same, FIG. 1 shows an exemplary embodiment 10 of the invention. Device 10 may be formed of any suitable material, such as titanium steel, stainless steel or nitinol. Device 10 has a first end, or proximal end, 12, a second end, or distal end, 14, a shaft 16 with an outer surface 17, and a center portion 18 between first end 12 and second end 14. A cutting point 19 is at second end 16 and a driving surface 20 is formed in the top of first end 12.

Cutting point 19 is preferred and helps cut through any bone left behind when the bone is drilled to receive device 10, as explained below.

Driving surface 20 in this embodiment has a Torx® drive configuration, although any suitable driving configuration may be used. Other driving configurations that may be used include slotted, Pozidriv®, Robertson, tri-wing, Torq®-set, spanner head, triple square and hex head.

Juxtaposed end 12 is preferably an outwardly-flared top portion 22, which aids in forming a compression fit in the opening formed in the bone.

Extending length wise in outer surface 17, preferably along the longitudinal axis of shaft 16, are grooves 24. As used herein, "extending length wise" means that each groove 24 is elongated and extends along the shaft with one end of the groove nearer the first end 12 and the opposite end of the groove nearer the second end 14, but grooves 24 may be formed at an angle and not necessarily formed along the longitudinal axis shaft 16, although that is preferred. Grooves 24 preferably have serrated edges that assist in boring the device 10 into and anchoring device 10 in the opening in a bone. Grooves 24 also may capture some debris left behind from the bone drilling process to create the opening created when device 10 is positioned into the opening.

Also formed in outer surface 17 is an annular ring or gap 26 and threads 28. Annular ring 26 has an outer diameter smaller than the outer diameter of the other components of device 10 except for the cutting point 18. The purpose of annular ring 26 is to collect debris that may be present or created when device 10 is inserted into the opening in the bone in order to make insertion of device 10 easier. Any suitable structure may be utilized for this purpose, and device 10 may have multiple annular rings 26.

Threads 28 in this embodiment are juxtaposed second end 14. Threads 28 extend outward from the outer surface 17 of shaft 16 by about 1-2 mm and are threaded into the opening formed in the bone. Any structure that can retain device 10 within a bone and prevent migration of deice 10 may be utilized for this purpose.

It is preferred that threads 28 are no more than 30%, and preferably no more than 25%, or about 15-25%, of the length of shaft 16. This is to reduce the torque required to screw device 10 into a bone, particularly a bone such as a metacarpal because it is narrow and relatively fragile. If too much torque were needed to insert device 10, the torque could damage the bone structure, or the driving surface 20 could be damaged, which could prevent complete insertion of device 10 into the opening.

Threads 28 could alternatively be juxtaposed first end 12, at one or more locations along center portion 18, or be at both first end 12 and second end 14. Alternatively, the threads could be displaced at one or more positions along center portion 18, and juxtaposed first end 12 and second end 14. Any location of the threads is suitable as long as the threads in their entity do not exceed the percentage of the overall shaft length set forth in the claimed inventions, and anchor device 10 in the opening.

FIGS. 2-2C depict a method for installing device 10 into a fractured metacarpal bone. In FIG. 2, the fracture in the bone is first aligned, and then a K-wire is inserted into the bone. A K-wire or pin is known I the art and is a sterilized, smooth steel pin used in orthopedics and other types of medical applications. It is available in different sizes as needed and provides structure, support and in one version has a diameter of about 0.040".

In FIG. 2A a cannulated drill, using the K-wire as a guide, drills an opening into the metacarpal bone, wherein the opening extends through the fracture and provides enough space on each side of the fracture to properly position device 10.

In FIG. 2B, device 10 is rotatably driven into the opening in the metacarpal bone. The outer diameter of the threads 28, and in this embodiment all of the structures of device 10 except annular gap 26 and cutting point 19, is slightly larger than the inner diameter of the opening in the bone. This provides bone material for threads 28 to thread into and provides a tight fit for device 10. However, device 10 could function properly if only threads 28 were slightly larger than the inner diameter of the opening, the other structures of device 10 except cutting point 19 and annular gap 26 were about the same size or slightly smaller than the inner diameter of the opening.

In this embodiment, the threads are ultimately anchored in the distal side of the metacarpal bone, which is the end opposite the side of the bone through which the opening starts. The serrations on the grooves 24 perform a scraping function that enables device 10 to be driven deeper into the bone with less torque. Internal debris from the procedure may be captured in the grooves 24 and/or annular gap 26 to help reduce the torque required to properly position device 10.

FIGS. 2D and 3 show device 10 in the metacarpal bone after the K-wire has been removed. Since device 10 is anchored in the metacarpal bone, there is no need for a second operation to remove it.

FIG. 4 shows an alternate embodiment of the invention, device 100. Device 100 is in all respects the same, and made from any suitable material and is inserted in an opening in a bone, as device 10 except that device 100 includes helical grooves 123. Helical grooves 123 assist in reducing torque and help to rotatingly drive device 100 into an opening in the bone when force is applied to the driving surface 120. Grooves 123 also collect debris as device 100 is being inserted, which, like annular gap 26, helps reduce the pressure against the outer surface 117 of shaft 116 and thus reduces the force required to position device 100 into the opening in the bone. Longitudinal grooves 124 preferably have serrated edges and are the same as previously described grooves 24 except that they are intermittent because they are intersected by helical grooves 123.

The structures and functions of the following components of device 100 have the same structures and functions of the components listed below with respect to device 10: first end, or proximal end, 112, and first end 12; second end, or distal end, 114 and second end 14; shaft 116 and shaft 16; outer surface 117 and outer surface 17; center portion 118 and center portion 18; cutting tip 119 and tip 19; driving surface 120 and driving surface 20; flared tip 122 and flared tip 22; and course threads 128 and course threads 28.

Referring to FIGS. 5-5C, a method of positioning device 100 into a bone is depicted. The positioning method is the same as that described with respect to device 10 except that debris collects in helical grooves 123 and there is no annular gap 16 (although device 100 could also include one or more annular gaps 16).

FIG. 6 shows device 10 positioned in a metacarpal bone.

Specific exemplary embodiments of the invention are described below:

EXAMPLE 1

A device for repairing a bone, the device for being received in the bone and comprising:
 a. a shaft having a length and an outer surface,
 b. a first end, a second end and a center portion between the first end and the second end;
 c. threads on the outer surface, wherein the threads comprise 25% or less of the shaft length; and
 d. a driving surface at the first end.

EXAMPLE 2

The device of example 1 wherein the device is comprised of one or more of nitinol, stainless steel and titanium steel.

EXAMPLE 3

The device of example 1 or 2 that has one or more grooves on the outer surface, the grooves extending length wise along the outer surface.

EXAMPLE 4

The device of example 3 wherein the shaft has a longitudinal axis and the one or more grooves on the outer surface extend along the longitudinal axis of the shaft.

EXAMPLE 5

The device of example 3 or example 4 wherein at least one of the one or more grooves extends at least half of the length of the shaft.

EXAMPLE 6

The device of any of examples 3-5 that has three or more grooves.

EXAMPLE 7

The device of any of examples 3-6 wherein at least one of the grooves has serrated edges.

EXAMPLE 8

The device of example 1 wherein the device has a center portion with an outer diameter and the threads have an outer diameter that is equal to or greater than the outer diameter of the center portion.

EXAMPLE 9

The device of any of examples 1-8 wherein the first end is flared outwards to provide a compression fit in an opening formed in a bone.

EXAMPLE 10

The device of any of examples 1-9 that further includes an annular gap between the second end and the first end, wherein the annular gap has a diameter, and the shaft on either side of the gap has a diameter, the diameter of the annular gap being less than the diameter of the shaft on either side of the annular gap, the gap for receiving debris generated when installing the device.

EXAMPLE 11

The device of example 10 wherein the annular gap diameter is 5-20% less than the diameter of the shaft on either side of the annular gap.

EXAMPLE 12

The device of any of examples 1-11 wherein there is a cutting surface at the second end.

EXAMPLE 13

The device of any of examples 1-12 that further includes one or more helical groves along at least part of the shaft.

EXAMPLE 14

The device of example 13 wherein at least one of the helical grooves has serrated edges.

EXAMPLE 15

The device of any of examples 1-14 wherein the threads are juxtaposed the second end.

EXAMPLE 16

The device of any of examples 1-14 wherein the threads are juxtaposed the first end.

EXAMPLE 17

The device of any of examples 1-14 wherein the threads are on the center portion.

EXAMPLE 18

The device of any of examples 1-14 wherein the threads are on two or more of the outer surface juxtaposed the second end, the outer surface juxtaposed the first end, and the center portion.

EXAMPLE 19

The device of any of examples 1-18 that includes a plurality of annular gaps on the outer surface of the shaft.

EXAMPLE 20

A method for repairing a metacarpal bone, the method comprising the steps of:
 a. drilling an opening in a fractured metacarpal bone, the opening extending through the fracture, the opening having an inner diameter;
 b. placing a device into the opening, the device having a shaft with a shaft length and an outer surface, a first end, a second end and a center portion between the first end and the second end, and threads on the outer surface, the threads being 25% or less of the shaft length, the threads having a thread diameter, the thread diameter being greater than the inner diameter of the opening;
 c. positioning the device into the opening by rotationally driving it using a driving tool, so that the device is positioned completely inside the opening on each side of the fracture in order to stabilize the bone.

EXAMPLE 21

The method of example 20 wherein the device is comprised of one or more of nitinol, stainless steel and titanium steel.

EXAMPLE 22

The method of any of examples 20-21 wherein the device has one or more grooves on the outer surface, the grooves extending length wise along the outer surface.

EXAMPLE 23

The method of example 22 wherein the shaft includes a longitudinal axis and at least one of the grooves on the outer surface extends along the longitudinal axis.

EXAMPLE 24

The method of example 22 or example 23 wherein at least one of the one or more grooves extends at least half of the shaft length.

EXAMPLE 25

The method of any of examples 22-24 wherein the device has three or more grooves.

EXAMPLE 26

The method of any of examples 22-25 wherein at least one of the grooves has serrated edges.

EXAMPLE 27

The method of example 20 wherein the device includes a center portion that has an outer diameter and the threads have an outer diameter that is equal to or greater than the outer diameter of the center portion.

EXAMPLE 28

The method of any of examples 20-27 wherein the first end of the device is flared outwards to provide a compression fit in the opening.

EXAMPLE 29

The method of any of examples 20-28 that further includes an annular gap between the second end and the first end, wherein the annular gap has a diameter, and the shaft on either side of the annular gap has a diameter, the diameter of the annular gap being less than the diameter of the shaft on either side of the annular gap, the annular gap for receiving debris generated when installing the device.

EXAMPLE 30

The method of example 29 wherein the annular gap diameter is 5-20% less than the diameter of the shaft on either side of the annular gap.

EXAMPLE 31

The method of any of examples 20-30 wherein the device includes a cutting surface at the second end.

EXAMPLE 32

The method of any of examples 20-31 wherein the device further includes one or more of helical groves along at least part of the shaft.

EXAMPLE 33

The method of example 32 wherein at least one of the helical grooves has serrated edges.

EXAMPLE 34

The method of any of examples 20-33 wherein the threads are juxtaposed the second end.

EXAMPLE 35

The method of any of examples 20-33 wherein the threads are juxtaposed the first end.

EXAMPLE 36

The method of any of examples 20-33 wherein the threads are on the center portion.

EXAMPLE 37

The method of any of examples 20-33 wherein the threads are on two or more of the outer surface juxtaposed the second end, the outer surface juxtaposed the first end, and the center portion.

EXAMPLE 38

The method of claim 32 wherein each of the helical grooves has serrated edges.

EXAMPLE 39

The device of claim 13 wherein each of the helical grooves has serrated edges.

Having thus described some embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

What is claimed is:

1. A method for repairing a metacarpal bone utilizing a device having a shaft with a shaft length, a cannula extending through the shaft, an outer surface, a first end, a second end, a center portion between the first end and the second end, threads on the outer surface and juxtaposed the second end, the threads being 25% or less of the shaft length, the threads having a thread diameter, and a first end having: an outer diameter, a driving surface, and not including apertures, the method comprising the steps of:
   (a) drilling an opening in a fractured metacarpal bone, the opening extending through a fracture, the opening having an inner diameter, wherein the thread diameter is greater than the inner diameter and the outer diameter of the first end is greater than the inner diameter;
   (b) inserting a guide wire into the opening;
   (c) positioning the device completely into the opening by (i) positioning the guide wire in the cannula, (ii) rotationally driving the device by engaging a driving end of a driving tool with the driving surface of the first end of the device and rotating the device using the driving tool until the device is positioned completely inside the opening on each side of the fracture in order to stabilize the bone.

2. The method of claim 1 wherein the device is comprised of one or more of nitinol, stainless steel and titanium steel.

3. The method of claim 1 wherein the device has one or more grooves on the outer surface of the center portion, the grooves extending length wise along the outer surface.

4. The method of claim 3 wherein the shaft includes a longitudinal axis and at least one of the grooves on the outer surface extends along the longitudinal axis.

5. The method of claim 3 wherein at least one of the one or more grooves extends at least half of the shaft length.

6. The method of claim 3 wherein the device has three or more grooves.

7. The method of claim 3 wherein at least one of the grooves has serrated edges.

8. The method of claim 1, wherein the center portion has an outer center diameter and the threads have an outer diameter that is greater than the outer center diameter of the center portion and the first end of the threads has an outer diameter that is greater than the outer center diameter.

9. The method of claim 1 wherein the first end of the device is flared outwards to provide a compression fit in the opening.

10. The method of claim 1 wherein the device includes a cutting surface at the second end.

11. The method of claim 1 wherein the device further includes one or more helical grooves along at least part of the center portion.

12. The method of claim 11 wherein at least one of the helical grooves has serrated edges.

13. The method of claim 12, wherein the device further includes a plurality of helical grooves and each of the helical grooves comprises serrated edges.

14. The method of claim 1 wherein the device further includes threads juxtaposed the first end.

15. The method of claim 14, wherein the device further includes threads on the center portion.

16. The method of claim 1 wherein the device further includes threads on the center portion.

17. The method of claim 1 that further includes the step of providing the device.

18. The method of claim 1, wherein the device does not include apertures extending through the shaft.

19. The method of claim 1 that further includes the step of providing the driving tool.

20. The method of claim 1, wherein the driving surface has a configuration selected from the group consisting of: Torx®, slotted, Pozidriv®, Robertson, tri-wing, Torq®-set, spanner head, triple square, and hex head.

* * * * *